United States Patent
Danker et al.

(10) Patent No.: US 7,465,817 B2
(45) Date of Patent: Dec. 16, 2008

(54) INOSITOLIZED PHOSPHOLIPIDS

(75) Inventors: Kerstin Danker, Berlin (DE); Michael Mickeleit, Berlin (DE); Dieter Mueller, Berlin (DE); Werner Reutter, Berlin (DE)

(73) Assignee: Charite-Universitats Medizin Berlin (DE)

( * ) Notice: Subject to any disclaimer, the term of this patent is extended or adjusted under 35 U.S.C. 154(b) by 68 days.

(21) Appl. No.: 10/535,834

(22) PCT Filed: Nov. 20, 2003

(86) PCT No.: PCT/EP03/13010

§ 371 (c)(1),
(2), (4) Date: Nov. 15, 2005

(87) PCT Pub. No.: WO2004/045623

PCT Pub. Date: Jun. 3, 2004

(65) Prior Publication Data

US 2006/0105996 A1    May 18, 2006

(30) Foreign Application Priority Data

Nov. 20, 2002    (EP)    ................................. 02025673

(51) Int. Cl.
*C07F 9/02*    (2006.01)

(52) U.S. Cl. .......................................... 554/78; 514/78
(58) Field of Classification Search .................... None
See application file for complete search history.

(56) References Cited

U.S. PATENT DOCUMENTS 4,697,031 A * 9/1987 Wissner et al. .............. 558/169
4,897,385 A * 1/1990 Wissner et al. ................ 514/77
5,637,304 A    6/1997 Salini

FOREIGN PATENT DOCUMENTS

WO    WO 01 72130 A    10/2001

OTHER PUBLICATIONS

Mickeleit et al., "Glc-PC, a new type of glucosidic phospholipid", Angew. Chem. Int. Ed. Engl., vol. 34, No. 23/24, 1995, pp. 2667-2669.
Mickeleit et al., "A glucose-containing ether lipid (Glc-PAF) as an antiproliferative analogue of the platelet-activating factor", Angew. Chem. Int. Ed. Engl., vol. 37, No. 3, 1998, pp. 351-353.

* cited by examiner

*Primary Examiner*—Deborah D Carr
(74) *Attorney, Agent, or Firm*—Rothwell, Figg, Ernst, Manbeck, P.C.

(57) ABSTRACT

The present invention relates to a phospholipid dreivative having a substituted or unsubstituted polyhydroxylated aliphatic carbocycle attached to the sn-1 or sn-2 position of the glycerol backbone, a pharmaceutical composition comprising said phospholipid, a method for preparing said phospholipid and a medicament comprising said phospholipid.

19 Claims, 5 Drawing Sheets

Lysophosphatidylcholine $R = C_{17}H_{35}, C_{15}H_{31}$

ET-18-OCH3

HePC

Glc-PC

Glc-PAF

Ino-PAF

Lysophosphatidylcholine

R = $C_{17}H_{35}$, $C_{15}H_{31}$

ET-18-OCH3

HePC

Glc-PC

Glc-PAF

Ino-PAF

INOSITOLIZED PHOSPHOLIPIDS

CROSS REFERENCE TO RELATED APPLICATION

This application is a 35 USC § 371 National Phase Entry Application from PCT/EP2003/013010, filed Nov. 20, 2003, and designated to the United States.

The present invention relates to a phospholipid derivative having a substituted or unsubstituted polyhydroxylated aliphatic carbocycle attached to the sn-1 or sn-2 position of the glycerol backbone, a pharmaceutical composition comprising said phospholipid, a method for preparing said phospholipid and a medicament comprising said phospholipid.

TECHNICAL BACKGROUND

Most cytostatic agents which are currently used in anticancer therapy either bind DNA directly (e.g. cisplatin or epirubicine) or target the cytoskeleton (e.g. vinblastine) or the mitotic spindle apparatus (e.g. taxol), thereby directly inhibiting cell cycle progression. For some years it has been well established that phospholipids are also involved in cell growth and intracellular signal transduction. (Cullis, P. R. et al. in Phospholipids and cellular regulation, I. Boca Raton (Ed.), CRC Press, 1-59 (1985); Nishizuka, Y., Science 258: 607-614 (1992)). Phospholipid analogs of high metabolic stability which interfere with these processes and act as proliferation inhibitors have been synthesized. These inhibitors act on a wide variety of cells, including prostate carcinoma, urothelial carcinoma of the bladder, hypernephroid carcinoma and teratocarcinomas (Berdel, W. E. et al., J. Natl. Cancer Inst. 66: 813-817 (1981); Berdel W. E. et al., J. Cancer Res. 43: 5538-5543 (1983); Herrmann, D. B. J., Neumann, H. A., Lipids 22: 955-957 (1987)), various human and murine leukemias, human brain tumors, human lung cancers (Berdel, W. E. et al., Cancer Res. 43: 541-545 (1983); Scholar, E. M. Cancer Lett. 33: 199-204 (1986), and fibrosarcomas (Houlihan, W. J. et al., Lipids 22: 884-890 (1987)). The exact mechanism of action of these phospholipid analogs remains to be elucidated. Primarily, however, the compounds are absorbed into cell membranes where they accumulate and interfere with a wide variety of key enzymes, most of which are membrane associated and are involved in lipid metabolism and/or cell signaling mechanisms (Arthur, G., Bittman, R. Biochim. Biophys. Acta 1390: 85-102 (1998)).

Besides their antiproliferative effects many phospholipid analogs are also potentially toxic, as shown by their lytic properties in cell culture experiments (Wieder, T. et al., J. Biol. Chem. 273: 11025-11031 (1998); Wiese, A. et al., Biol. Chem. 381: 135-144 (2000)), and therefore efforts have been made to synthesise phospholipid analogs with high antiproliferative capacity but low cytotoxic side effects.

The development of phospholipid analogs as antiproliferative agents resulted from the observation that lysophosphatidylcholine (LPC; FIG. 1) played a role in host defense mechanisms (Burdzky, K. et al., Z. Naturforsch. 19b: 1118-1120 (1964). Most commonly used phospholipid analogs are derivatives of lysophosphatidylcholine and lysoplatelet-activating factor (lyso-PAF). Edelfosine, 1-O-octadecyl-2-O-methyl-sn-glycero-3-phosphocholine (ET-18-OCH3; FIG. 1), is a PAF-derived compound that specifically inhibits the growth of tumor cells, tumor cell invasion, and metastasis and enhances the tumoricidal capacity of macrophages (Houlihan, W. J. et al., Med. Res. Rev. 15: 157-223 (1995)). There are also structurally similar long-chain glycerol-free phosphobase agents, such as hexadecyl-phosphocholine (HePC; FIG. 1), the only compound with therapeutic potential. HePC is currently used for the topical treatment of skin metastases in breast cancer patients (Unger, C. et al., Progr. Exp. Tumor Res. 34: 153-159 (1992); Clive, S., Leonard, R. C. F., Lancet 349: 621-622 (1997)) and visceral leishmaniasis (Jha, T. K. et al., N. Engl. J. Med. 341: 1795-1800 (1999). Due to negative side effects such as high cytotoxicity, efforts have been made to synthesise phospholipid analogs that are less cytotoxic.

Therefore, a novel strategy was followed by introducing sugars or sugar alcohols into the glycerol backbone. The introduction of glucose into the sn-2 position gave rise to glyceroglucophosphocholine (Glc-PC) as well as 1-O-octadecyl-2-O-α-D-gluco-pyranosyl-sn-glycero-3-phosphocholine (Glc-PAF; FIG. 1) (Mickeleit, M. et al., Angew. Chem. Int. Ed. Engl. 34: 2667-2669 (1995); Mickeleit, M. et al., Angew. Chem. Int. Ed. Engl. 37: 351-353 (1998)). Both compounds are water-soluble and display growth inhibitory properties at non-toxic concentrations as discussed further below.

The use of sugar-containing phospholipid analogs has also been described by other groups. Replacement of the sn-3 phosphocholine residue by different monosaccharides results in more effective analogs, compared to non-glycosidated, phosphocholine-containing compounds (Marino-Albernas, J. R. et al., J. Med. Chem. 39: 3241-3247 (1996); Samadder, P., Arthur, G. Cancer Res. 59: 4808-4815 (1998)).

On the other hand it is well known that the metabolism of phosphatidylinositol—having inositol esterified with the phosphate group—liberates intracellular messengers such as inositol-1,4,5-trisphosphate (Lehninger, A. L. et al., Prinzipien der Biochemie, Tschesche, H. (ed.), $2^{nd}$ edition, Spektrum Akademischer Verlag, 298 (1994)). Therefore, phosphatidylinositol participates in intracellular signal transduction. Inositol containing phospholipids are also known—although without exact structural information and in contexts differing from the one here—from WO 01/82921 A2, WO 02/04959 and JP 2002010796 A.

However, it remained desirable to find phospholipids which were more effective than the ones described before and which—at the same time—had none of the drawbacks as described above.

BRIEF DESCRIPTION OF THE INVENTION

Surprisingly, the inventors of the present invention found that introduction of the sugar alcohol inositol, which results in inositol-PAF (Ino-PAF), influences proliferation of cells much more powerfully than the glucose-containing analog. Therefore, the present invention provides a novel class of glycerophospholipids in which sugar alcohols instead of a fatty acid molecule have been incorporated into the phosphatidylcholine molecule.

The aforementioned glycerophospholipids show a remarkable effect on proliferation and other physiological processes. In particular the present invention provides (1) a phospholipid having a substituted or unsubstituted polyhydroxylated aliphatic carbocycle attached to the sn-1 or sn-2 position of the glycerol backbone;

(2) a pharmaceutical composition comprising the phospholipid as defined under (1) above;

(3) a method for preparing the phospholipid as defined under (1) above which comprises reacting a glycerol precursor compound with a precursor compound of the activated substituted or unsubstituted polyhydroxylated aliphatic carbocycle compound (to therewith link said carbocycle compound directly or through a linker molecule to the oxygen atom of the glycerol backbone);

(4) use of a phospholipid as defined in (1) above for preparing a medicament for the treatment of prostate carcinoma, urothelial carcinoma of the bladder, hypernephroid carcinoma, teratocarcinomas, human and murine leukemias, brain tumors, lung cancers, fibrosarcomas, and hyperproliferative diseases of the skin; and (5) a method of treatment of prostate carcinoma, urothelial carcinoma of the bladder, hypernephroid carcinoma, teratocarcinomas, human and murine leukemias, brain tumors, lung cancers, fibrosarcomas and hyperproliferative diseases of the skin comprising administering a phospholipid as defined in (1) above to a patient.

DETAILED DESCRIPTION OF THE INVENTION

Figure 1:
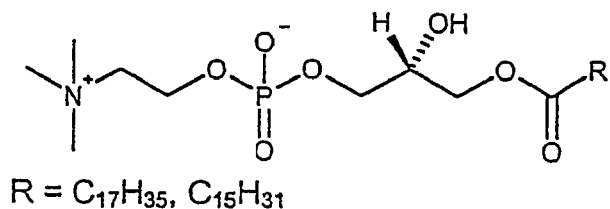
FIG. 1 shows the chemical structures of the phospholipid analogs mentioned in the application.
Figure 1:
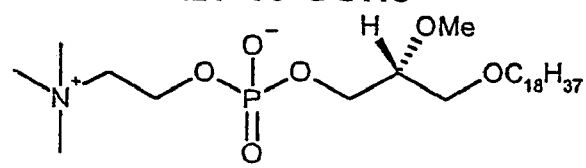
Figure 1:
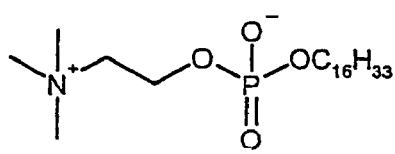
Figure 1:
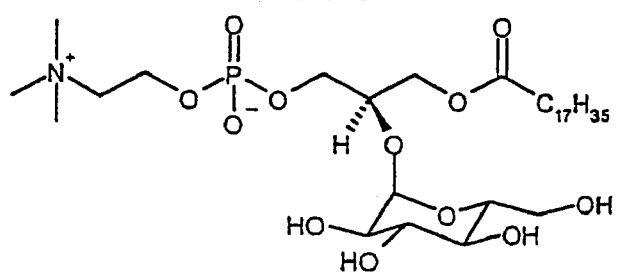
Figure 1:
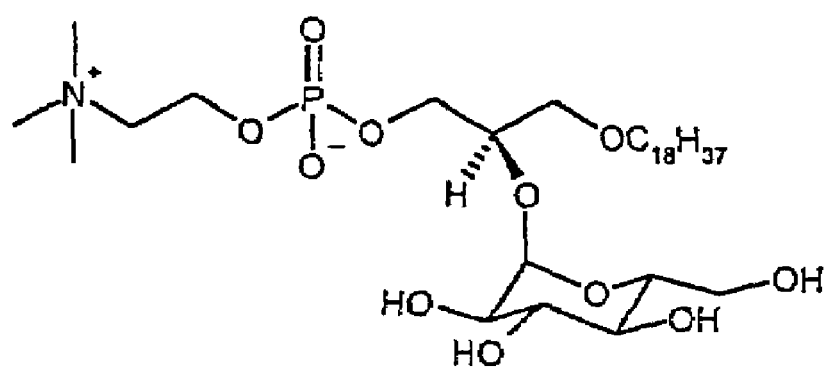
Figure 1:
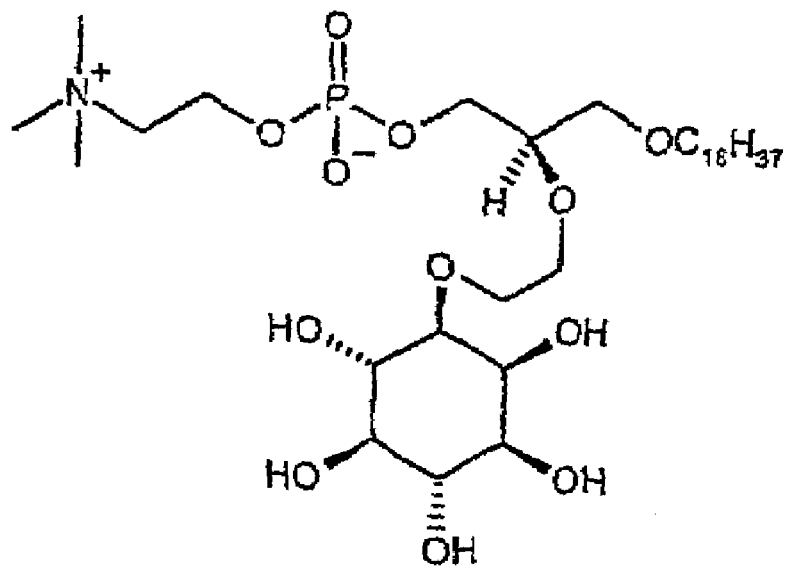

The search for specific anticancer drugs which do not interfere with DNA synthesis, or influence the cytoskeleton, but affect other targets, leading, for example, to remodeling the structure and function of plasma membranes, is considered a promising future line of research. In addition to the already established antitumor phospholipid analogs, a novel class of synthetic phospholipids has been described: the sugar alcohol-containing analogs of lysophosphatidylcholine, such as Ino-PAF. It was shown that these types of compounds inhibit cell proliferation and activate cell matrix adhesion in vitro.

Although the exact mechanisms of action of the compounds are not known, it seems clear that they affect other signaling pathways other than those influenced by the conventional phospholipid analogs. Therefore, these compounds may also be used in combination with other known cytostatic drugs to counteract drug resistance.

Within the phospholipids of present invention the three OH-groups of the glycerol backbone are referred to—in consecutive order—with the designators sn-1, sn-2 -and sn-3 as widely accepted in the field of chemistry. The term "phospholipid" within the meaning of the present invention refers to a compound consisting of a glycerol backbone phosphorylated in the sn-3 position, being further substituted and having amphiphilic properties as generally accepted in the art.

In a preferred embodiment the phospholipid of the invention has the formula (I)

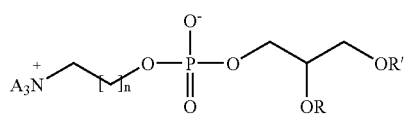

(I)

wherein
(i) A are independently optionally substituted $C_{1-6}$ alkyl moieties or two A residues may form an optionally substituted 5- to 7-membered ring,
(ii) one of R and R' is a first residue comprising a polyhydroxylated aliphatic carbocycle or a derivative thereof being directly or through a linker molecule connected to the oxygen atom of the glycerol backbone, and the other is a second residue selected from optionally unsaturated and/or optionally substituted $C_{1-20}$ alkyl, optionally unsaturated and/or optionally substituted $C_{2-26}$ acyl and hydrogen, and
(iii) n is an integer ranging from 1 to 5.

The term "alkyl" or "alkyl moiety" refers to any linear or branched constitutional isomer of a residue of an alkane $C_n$ with n being an integer refers to the number of carbon atoms of an alkyl chain, i.e. the number of CH, $CH_2$ and $CH_3$ groups. The term "optionally unsaturated alkyl" or "alkene" refers to a mono, di-, tri- or polyunsaturated alkene.

The term "optionally unsaturated and/or optionally substituted $C_{1-20}$ alkyl" within the present invention thus includes lower, e.g. $C_{1-6}$ alkyl groups such as methyl, ethyl, n-propyl, isopropyl, n-butyl, sec-butyl, tert-butyl, n-pentyl, sec-pentyl, neo-pentyl, n-hexyl, etc., and also fatty acid derived (e.g. $C_{14-20}$) alkyl and alkenyl groups such as myristyl, palmityl, stearyl, arachidyl, oleyl, linayl, linolenyl, arachidonly, etc.

The term "acyl" refers to any linear or branched constitutional isomer of a carboxylate residue, i.e. an alkane or alkene carboxylic acid residue. Among the alkane carboxylic acid residues according to the present invention lauroyl (n-dodecanoyl), myristoyl (n-tetradecanoyl), palmitoyl (n-hexadecanoyl), stearoyl (n-octadecanoyl), arachidoyl (n-eicosanoyl) and lignoceroyl (n-tetracosanoyl) are preferred. Among the alkene carboxylic acid residues according to the present invention palmitoleinoyl, oleoyl, linoloyl, linolenoyl and arachidonoyl (5,8,11,14-eicosatetraenoyl) are preferred.

The $C_{1-6}$ alkyl moieties within the definition of A includes those mentioned above. The 5- to 7-membered ring may—besides the nitrogen atom—comprise further heteroatoms such as oxygen, sulfur and nitrogen. Particularly preferred rings within the definition of A are pyrrolidinyl, piperidinyl, morpholinyl, etc.

The optional substituents of the groups within the definition of A, R and R' include, but are not limited to, hydroxy, halogen (fluorine, chlorine, bromine, iodine), oxo, $C_{1-6}$ alkoxy, carboxy. The substituents of the polyhydroxylated aliphatic carbocycle include esters, acetates and thers of the hydroxy functionalities and oxo and halogen substituents at the C-atoms of the carbocycle.

It is particularly preferred in the compound of formula (I) above that A is selected from $CH_3$, $C_2H_5$, $C_3H_7$ and $CH(CH_3)_2$, preferably A is $CH_3$. It is moreover preferred that R is the first residue, i. e. that the polyhydroxylated aliphatic carbocycle is located at the sn-2 position and/or that the second residue is a $C_{10-20}$ alkyl, preferably a $C_{16}$ or $C_{18}$ alkyl group. Still further preferred is that the first residue has one of the following formulas:

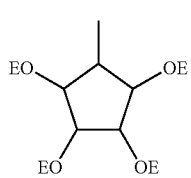

(II)

-continued

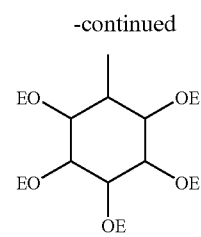
(III)

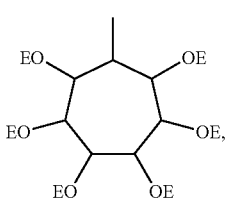
(IV)

wherein E is selected from H, $C_{1-4}$ alkyl, $C_{2-4}$ acyl, a carbohydrate moiety and the like, preferably E is H.

Finally, it is preferred that n=1.

The linker (hereinafter sometimes designated, "L") connecting the polyhydroxylated aliphatic carbocylce with the glycerol backbone can be any functional structure enabling stable linkage. Suitable linkers are (poly)ethers, (poly)peptides, glycosides, (poly)esters, alkyl or alkenyl spacers, etc., with (poly)ether being most preferred.

In a more preferred embodiment the phospholipid is a residue of formula (III). The residue of formula (III) includes cis-inositol, epi-inositol, allo-inositol, neo-inositol, myo-inositol, muco-inositol, chiro-inositol or scyllo-inositol, and preferably is myo-inositol. In an even more preferred embodiment of the invention the phospholipid corresponds to formula (V)

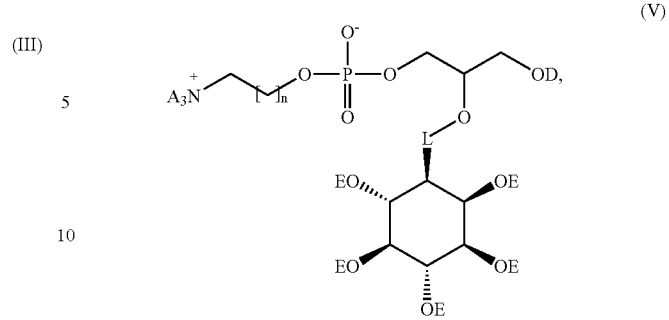
(V)

wherein D is a second residue as defined above and E, A, L and n are as defined above. Most preferred is the compound Ino-Paf (or "Ino-C2-PAF" as it is occasionally referred to) shown in FIG. 1.

It is understood that any of the phospholipids of the present invention which contain stereogenic carbon atoms include the corresponding racemates as well as all possible configurational isomers resulting from stereogenic carbon atoms defined in the R- or S-form according to the Cahn-Ingold-Prelog rules for nomenclature. In particular, the configuration of the carbon atom in the sn-2 position of the glycerol backbone of the phospholipid can be R or S, preferably is R.

It is further understood that any of the phospholipids of the present invention which contain carbon-carbon double bonds comprise all possible configurational isomers resulting from E-/Z-isomerism.

The method for preparing of the phospholipid of the invention preferably comprises reacting a precursor compound of formula (I)

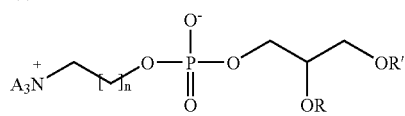
(I)

wherein at least one of OR or OR' represents a leaving group or —O⁻ (or an appropriately derivatized linker moiety attached to the respective O-atom) and the other variables are as defined above, or a protected form thereof, with a functional form of the first residue. The particularly preferred compound Ino-PAF can be synthesized according to the following reaction scheme:

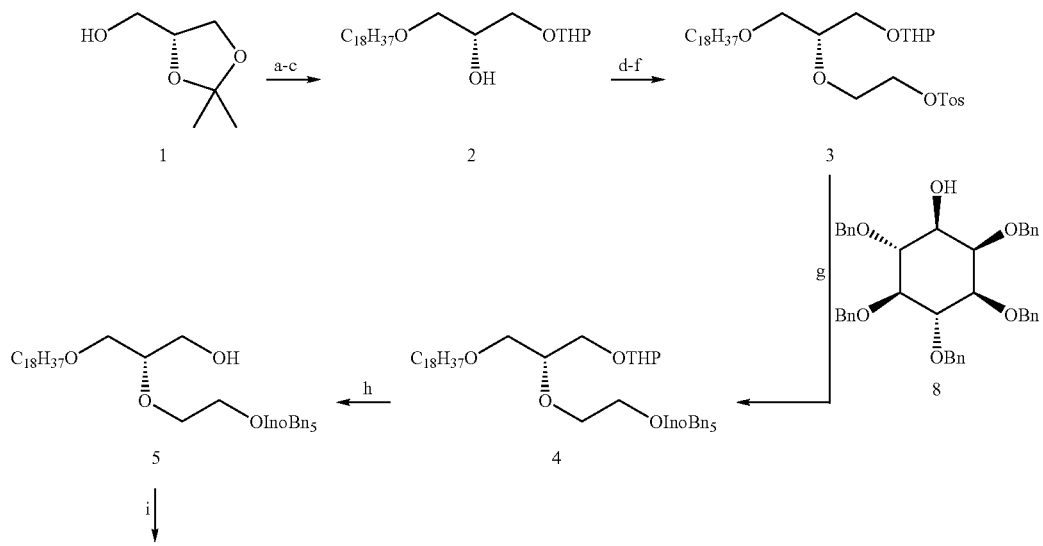

-continued

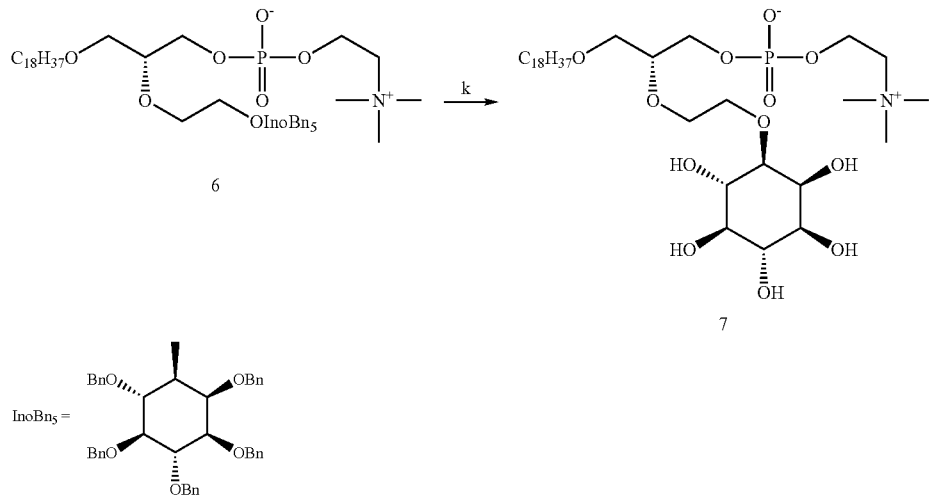

(a) C$_{18}$H$_{37}$Br, NaH; (b) AcOH; (c) DHP, p-TosOH; (d) allylbromide, NaH;
(e) i: O$_3$, ii: NaBH$_4$; (f) p-TolSO$_2$Cl, NEt$_3$, DMAP; (g) penta-benzylinositiol 8,
KHMDS, 18-Cr-6; (h) pyridinium p-toluenesulfonate; (i) i: POCl$_3$, NEt$_3$
ii: choline tosylate iii: NaHCO$_3$, H$_2$O; (k) H$_2$, Pd/C 5%

Ino-PAF 7 can be synthesized form (R)-(−)-1,2-O-isopropylideneglycerol 1, which is readily available from D-mannitol in 3 steps. Initially the glycerol 1 is converted to the secondary alcohol 2 by etherification with stearylbromide followed by the cleavage of the isopropylidene group under acidic conditions and protection of the resulting primary alcohol group as a tetrahydropyranoyl ether. In order to introduce the C$_2$-linker fragment alcohol 2 is etherified with allylbromide. The resulting allyl ether is treated with ozone and subsequently reduced by sodium borohydride. The reaction of the obtained primary alcohol with p-toluenesulphonylchloride gives the tosylate 3. This tosylate 3 is substituted by 1,2,3,4,5-O,O,O,O,O-pentabenzyl-myo-inositol 8, which was previously synthesized from myo-inositol via a 6 step sequence (Gigg, R., Warren, C. D., Chem. Soc. (C):2367-2371 (1969)). The resulting inositol ether 4 is deprotected under acidic conditions to give the primary alcohol 5.

Subsequent reaction of the alcohol 5 with phosphorylchloride and choline tosylate generates the phosphatidylcholine 6. Final hydrogenation of 6 gives the target compound Ino-PAF 7.

For the purposes of the present invention the terms "Ino-PAF" and "Ino-C2-PAF" are used synonymously, i.e. designate the same compound.

The "pharmaceutical composition" and "medicament" within the meaning of the present invention comprises one or more of the phospholipids according to the present invention and optionally a pharmaceutically acceptable carrier, diluent or the like. Among such pharmaceutically acceptable carriers are lipid nanosus pensions, liposomes, biodegradable microparticles and the like.

The impact of glycosidation in the glycosidated phospholipid analogs was determined in serum-free cell cultures of human keratinocytes (HaCaT cells) and a squamous carcinoma cell line (SCC-25). It was shown that Glc-PC as well as Glc-PAF inhibited cell proliferation of HaCaT cells in the μmolar range, with half-inhibitory concentrations (IC$_{50}$) below the respective LD$_{50}$ (Table 1).

TABLE 1

The cytotoxic and antiproliferative effects on HaCaT cells of the different glycosidic phospholipid analogues. Viability was determined by the LDH assay. Cell proliferation was measured by use of the cell proliferation ELISA, based on the incorporation of BrdU (Roche).

| Phospholipid analog | Proliferation (IC$_{50}$) | Viability (LD$_{50}$) |
|---|---|---|
| Glc-PC | 9 | 50 |
| Glc-PAF | 5 | 9 |
| Ino-PAF (=Ino-C2-PAF) | 1.8 | 15 |
| HePC | 4.5 | 6 |

Direct comparison of the cytotoxic and the antiproliferative capacities revealed that Glc-PC in particular displays a large difference between the LD$_{50}$ and its IC$_{50}$, while in cells treated with the antitumor phospholipid HePC, the IC$_{50}$ is very close to the LD$_{50}$.

In SCC-25 cells the antiproliferative effects of the glycosidated phospholipid analogs is much stronger. In particular, Glc-PAF acts in the sub-μmolar range on these tumor cells.

The toxicity of Glc-PAF and Glc-PC is mediated by intercalation of the substances into cellular membranes. Using fluorescence resonance energy transfer (FRET) spectroscopy it was clearly demonstrated that both compounds are intercalated into liposomes and that the intercalation depends on the length of the alkyl side chain. At high concentrations, this leads to the formation of lesions in the plasma membrane and finally to rapid lysis of the cells (Wiese, A. et al., Biol. Chem. 381: 135-144 (2000)). The lower cytotoxicity of Glc-PC as compared to Glc-PAF, which is also reflected in the FRET analysis, might be attributed to the higher stability and rigidity of ether lipids (Eibl; H., Angew. Chem. 96: 247-262 (1996)).

The antiproliferative effects of the phospholipid analogs did not seem to be a simple consequence of their lytic properties, since, as already mentioned, the proliferation of HaCaT cells was inhibited at non-toxic concentrations.

Introduction of inositol into the sn-2 position of lyso-PAF in place of glucose (Ino-PAF) enhances the antiproliferative effect ($IC_{50}$=1.7 µM) and reduces the toxic effect, compared to Glc-PAF ($LD_{50}$>10 µM) (Fischer et al., unpublished data). For this reason Ino-PAF is a promising candidate for the development of an antiproliferative drug.

Development and differentiation of keratinocytes, finally leading to the formation of a well stratified epidermis, involves modifications of cell proliferation and of the adhesive interactions with other cells and extracellular matrix components. In both malignant and benign hyperproliferative disorders of the epidermis, both cell proliferation and adhesion are impaired.

Cell matrix adhesion is mediated by integrins, a family of heterodimeric cell surface receptors. Binding of integrins to molecules of the extracellular matrix leads to induction of signal transduction pathways including activation of the mitogen-activated protein kinases, Rho A and protein kinase C (outside-in signalling). Conversely, signals from inside the cell can modulate the integrin affinity for its ligand, leading to changes in adhesion and migration of the cell (inside-out signalling).

Figure 3:
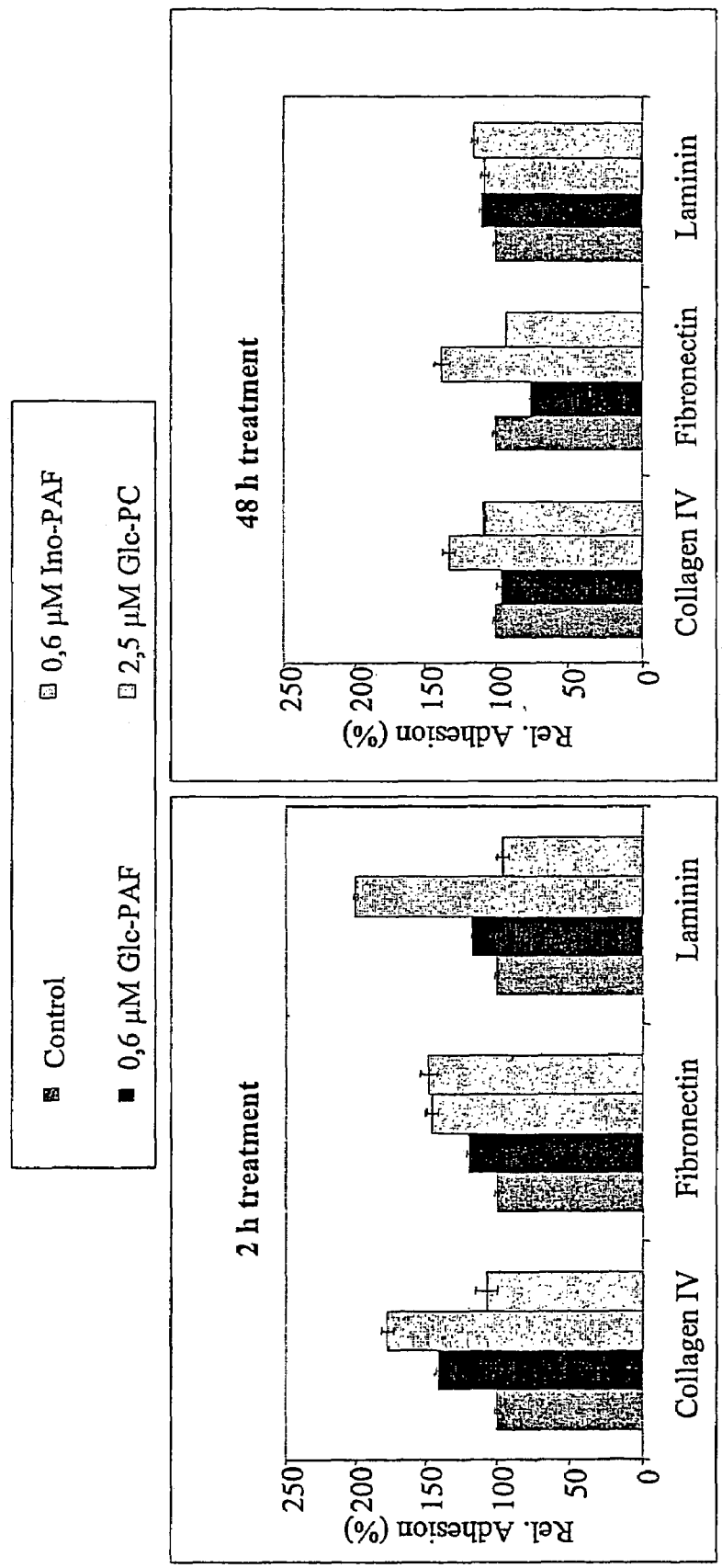
FIG. 3 summarizes the cell matrix adhesion activity in testing of Ino-PAF (in comparison with other phospholipid analogs) in the HaCaT cell test model given in Example 3.

In the skin, integrins play an important role in the establishment of the functional integrity of the dermo-epidermal junction (Kaufmann, R. et al., Hautarzt 41: 256-261 (1990)), and it has been shown in various reports that the expression pattern of integrins is altered in hyperproliferative diseases of the skin (for review see: De Luca, M. et al., J. Dermatol. 21, 821-828 (1994)). Besides their effect on cell proliferation, glycosidated phospholipid analogs influence cell matrix adhesion of keratinocytes. Treatment of HaCaT cells for 2 h with Glc-PAF and mainly Ino-PAF increases cell adhesion to the extracellular matrix components fibronectin, laminin and collagen IV (FIG. 3). This effect can also be observed after a longer exposure of 48 h to the glycosidated ether lipids (Fischer et al., unpublished data). This is in clear contrast to the action of the antiproliferative drug HePC that has been shown to reduce cell matrix adhesion to all mentioned matrix components (Schoen, M. et al., Brit. J. Dermatol. 135: 696-703 (1996)).

The increase of matrix adhesion is not accompanied by an increase of β1 integrins at the cell surface. This leads to the conclusion that activation of cell matrix binding may be mediated by an inside-out mechanism triggered by the intercalation of the phospholipid analogs into the cell membrane. Another possibility is that the altered membrane composition could induce directly a conformational change of the integrin receptor, leading to activation and/or clustering of integrin heterodimers.

Since phospholipid analogs can accumulate in the plasma membrane, they are presumed to have an impact on transmembrane signal propagation. It has been shown that ether lipids like Et-18-0CH3 inhibit phospholipid-modifying enzymes, such as phosphatidyl inositol-dependent-phospholipase C (PI-PLC) and phosphatidyl inositol-3-kinase (PI 3-kinase) (outlined in detail by Arthur, G., Bittman, R., Biochim. Biophys. Acta 1390: 85-102-(1998)).

The exact mechanism of action of glycosidated phospholipids has still to be elucidated. Their influence on proliferation and adhesion might result from the intercalation into the lipid matrix of the target cell, thus influencing signal transduction processes and subsequently biological responses.

Signal transduction pathways that are modulated by glycosidated phospholipid analogs are not well investigated. Various isoenzymes of protein kinase C (PKC) play an essential role in the control of cell proliferation (Clemens, M. J. et al., J. Cell Sci. 103: 881-887 (1992)). Treatment of HaCaT cells with Glc-PC at non-toxic concentrations increases the activity of this enzyme by up to 70% (Mickeleit, M. et al., Angew. Chem. Int. Ed. Engl. 34: 2667-2669 (1995)). At higher concentrations of Glc-PC the increase is abolished. Even high, toxic concentrations of Glc-PC do not inhibit PKC activity in vitro. This is in contrast to many known antiproliferative agents.

Glc-PAF has been shown to cause apoptosis at low but antiproliferative concentrations. The number of apoptotic cells shows a concentration-dependent increase. At higher toxic concentrations there is a marked decrease in the number of apoptotic cells, as determined by the presence of cytosolic nucleosomes. This also indicates that the cells are damaged by lysis at these higher concentrations (Mickeleit, M. et al., Angew. Chem. Int. Ed. Engl. 37, 351-353 (1998)).

The advantages of Ino-PAF can be summarized as follows:

It shows stronger antiproliferative effects than the therapeutically used HePC.

The cell matrix adhesion is increased after incubation with InoPAF or HePC, but the latter shows a delayed onset of action.

The increased adhesion is hot due to an increased expression of β1 integrins on the cell surface, but to an induced clustering of integrins.

The Treatment of HaCaT cells with Ino-PAF has different effects: a rapid one within the first 2 h that acts on adhesion and a slower one after 48 h that effects migration and proliferation.

The pharmaceutical composition of the invention is thus suitable for the treatment of prostate carcinoma, urothelial carcinoma of the bladder, hypernephroid carcinoma, teratocarcinomas, human and murine leukemias, brain tumors, lung cancers, fibrosarcomas and hyperproliferation diseases of the skin and the like.

The invention is further explained by the following examples, which are, however, not to be construed as limiting the invention.

EXAMPLES

Example 1

Synthesis of Ino-PAF

Materials, Methods and Abbreviations

Moisture sensitive reactions were carried out under a protective atmosphere (nitrogen, inert gas or drying tube as appropriate) using anhydrous solvents. Flash column chromatography refers to column chromatography on silica gel 60 (ASTM, 40-63 µm or 230-400 mesh, respectively) under pressure. The mixture of a solvent A with a solvent B is referred to as A-B, and the concentration by volume of solvent A in the mixture A-B is given as x % so that the solvent system is fully characterised by x % A-B.

| | |
|---|---|
| DCM | dichloromethane |
| DMAP | N,N-dimethyl-4-aminopyridine |
| DMF | N,N-dimethylformamide |
| equiv | equivalent |
| EtOH | ethanol |
| h | hour |
| MeOH | methanol |
| PPTS | pyridinium p-toluenesulfonate |
| p-TsCl | p-toluenesulfonyl chloride |
| p-TsOH | p-toluenesulfonic acid |
| rt | room temperature |

| | |
|---|---|
| sm | starting material |
| THP | tetrahydropyrane |
| THF | tetrahydrofurane |

The wavenumbers of maximum absorbance observed by IR (infrared) spectroscopy are reported as $\nu_{max}$ in the unit $cm^{-1}$.

Chemical shifts observed by $^1$H-NMR (nuclear magnetic resonance) spectroscopy are reported as $\delta_H$ in the unit ppm.

1.1: Preparation of 5,6-O-Isopropylidene Ascorbic Acid 1a

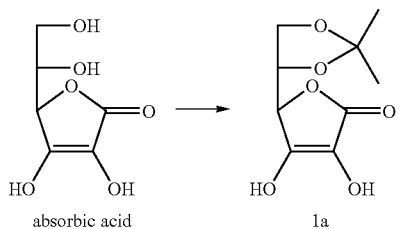

L-Ascorbic acid (Bronson Pharmaceuticals; 10 g, 55 mmol, 1 equiv) was mixed with acetone (40 ml, 0.55 mol, 1 equiv) and acetyl chloride (1 ml, 15 mmol, 0.27 equiv) and the slurry obtained was stirred at rt for 2-3 h. After standing at 7° C. for 4-8 h the solid was filtered off and washed with a small amount of cold acetone. Drying for a short period of time under reduced pressure gave the crude product (9.63 g, 81%); mp 195-200° C. A trace amount of residual acetic acid caused hydrolysis if the product was exposed to the ambient atmosphere. The crude product was recrystallized from acetone/hexane to yield the title compound 1a; mp 214-218° C. (decomposition) (literature (Jung, M. E.; Shaw, T. E., J. Am. Chem. Soc. 102:6304-6311 (1980)): mp 217-222° C. (decomposition); $\nu_{max}$ (KBr) 3300, 3000, 1720, 1630, 1300 (br), 1100 $cm^{-1}$; $\delta_H$ (250 MHz, acetone-$d_6$, $Me_2SO$-$d_6$) 3.9-4.65 (m, 6H, CHO and OH), 1.35 (s, 6H, CH); $\delta_H$ (250 MHz, $CDCl_3$, $Me_2SO$-$d_6$) 6.15 (br s, 2H, OH), 3.98-4.62 (m, 4H, CHO), 1.35 (s, 6H, $CH_3$).

1.2: Preparation of (R)-Glycerol Acetonide 1

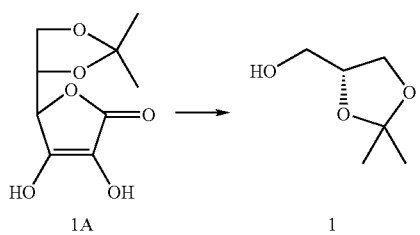

A solution of 1a (4.1 g, 19 mmol) in ethanol (350 ml) was added over 1 h to a stirred solution of $NaBH_4$ (0.72 g, 19 mmol) in ethanol (50 ml). The slightly cloudy solution was then stirred at rt for an additional 4 h, during which the pH of the reaction mixture was made basic by the addition of NaOH followed by the addition of aqueous NaOH (1 N; 50 ml). The mixture obtained was stirred overnight at rt, and the pH was then adjusted precisely to neutral by the dropwise addition of concentrated aqueous HCl under vigorous stirring. The solvents were removed in vacuo adding ethanol several times in order to remove residues of water by azeotropic distillation until a dry, white and powdery solid was obtained, which was mixed with ethyl acetate (200 ml) and cooled to 0° C. Lead tetraacetate (recrystallized from acetic acid; 29.5 g, 0.66 mol) was added in one portion. The resulting brown to yellow slurry was stirred 1-1.5 h at 0° C. and then 1-2 h at rt. After cooling to 0° C. the slurry was filtered through a pad of Celite®. The filtrate was cooled again and the cold, yellow solution was then added over 30 min to a cooled solution of $NaBH_4$ (7.2 g, 19 mmol) in EtOH (150 ml), which turned dark grey upon the addition of the ethyl acetate solution and might need occasional addition of EtOH to aid stirring and minimize foaming. After the addition was completed the grey solution was allowed to warm to rt while stirring for 2-2.5 h, then made basic by adding NaOH followed by aqueous sodium hydroxide (1 N, 100 ml). The mixture obtained was stirred for 30 min at rt, then diethyl ether (100 ml) was added, the layers were separated, and the aqueous layer was extracted with diethyl ether (2×50 ml). The combined organic layers were washed with brine (25 ml), dried ($NaSO_4$) and concentrated under reduced pressure at rt to a volume of about 50 ml. Diethyl ether (100 ml) was added, the aqueous phase was saturated with NaCl, and the layers were separated. The aqueous layer was extracted with diethyl ether (4×50 ml). The combined organic layers were dried ($NaSO_4$) and concentrated. Any residual water was then distilled off by forming an azeotrope with acetone (25, ml) and (R)-glycerol acetonide 1 (1.32 g, 53%) was obtained as a clear liquid. The product was further purified by flash column chromatography (50 g of silica gel; elution with DCM (350 ml) removed impurities; 5% methanol-DCM (500 ml)) to yield (R)-glycerol acetonide 1 (1.26 g, 97%); $\nu_{max}$ 3420, 2950, 1380, 1260, 1215, 1160, 1050 $cm^{-1}$; $\delta_H$ (250 MHz, $CDCl_3$) 3.6-4.4 (m, 5H, CHO), 2.95 (br s, 1H, OH), 1.43 (s, 3H, $CH_3$), 1.38 (s, 3H, $CH_3$); a sample of 184 mg was distilled (24° C. (0.5 torr)) to yield 169 mg of a clear liquid which was dissolved in 1.00 ml of MeOH for measurement of optical rotation: $[\alpha]^{24.8}_D$ −10.76 (literature (Jung, M. E.; Shaw, T. E., J. Am. Chem. Soc. 102:6304-6311 (1980)): $[\alpha]_D$+10.7 for opposite enantiomer, $[\alpha]_D$ −13.2 for neat sample), $[\alpha]_{578}$ −11.27, $[\alpha]_{546}$ −12.99, and $[\alpha]_{436}$ −23.59.

1.3: Preparation of Octadecyl Ether 1b

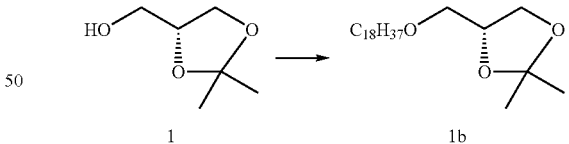

To a stirred suspension of NaH (80%; 0.55 g, 17.4 mmol, 2 equiv) in THF (20 ml) was added dropwise a solution of (R)-glycerol acetonide 1 (1.15 g; 1 equiv) in THF (20 ml). After that octadecyl bromide (5.8 g, 17.4 mmol, 2 equiv) dissolved in THF (25 ml) was added dropwise and the mixture obtained was stirred overnight at 80° C. The reaction mixture was cooled to 0° C. and water was added. The resulting mixture was concentrated and the residue was extracted with water and diethyl ether and the combined extracts were dried ($MgSO_4$). The crude product obtained was further purified by flash column chromatography (10% ethyl acetate-n-hexane) to yield the title compound 1b (2.03 g, 5.28 mmol, 61%).

1.4: Preparation of Diol 1c

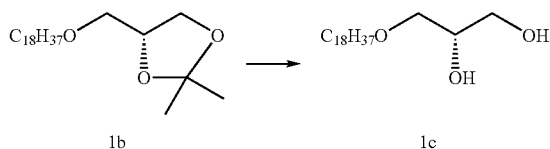

As suspension of acetonide 1b (2.03 g, 5.28 mmol) in a mixture of acetic acid (150 ml) and water (50 ml) was stirred for 3 h at 60° C. After that the solvents were removed and the residue was azeotropically distilled with toluene three times in order to completely to remove any traces of water and acetic acid. The title compound 1c (1.82 g, 5.28 mmol, quantitative) was obtained as a white solid; $R_f$ 0.2 (50% ethyl acetate-n-hexane).

1.5: Preparation of Alcohol 2

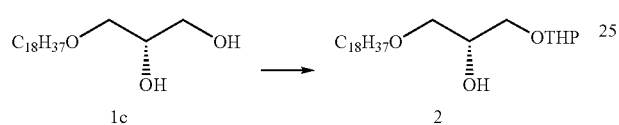

To a stirred suspension of diol 1c (2.5 g, 7.25 mmol, 1 equiv) in DCM (100 ml) was added p-TsOH at rt followed by the dropwise addition of a solution of dihydropyrane (0.65 ml, 1 equiv) in DCM (30 ml). After 30 minutes the reaction was quenched by the addition of saturated aqueous $NaHCO_3$. The mixture obtained was extracted with water and DCM and the combined organic extracts were dried ($MgSO_4$). The crude product (a mixture of diol 1b and the corresponding mono- and di-THP ether) was purified by column chromatography (25% ethyl acetate-n-hexane) to give the title compound 2 (940 mg, 2.72 mmol), unreacted sm and the corresponding di-THP ether, which was recycled to the sm by reaction with $NH_4Cl$ in MeOH at 80° C. overnight. The reaction described before was repeated once to yield the title compound (1.88 g, 4.38 mmol, 60%); $R_f$ 0.1 (25% ethyl acetate-n-hexane).

1.6: Preparation of Allyl Ether 2a

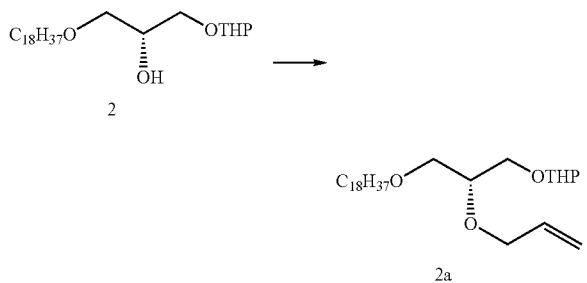

A solution of alcohol 2 (2.58 g, 6.01 mmol, 1 equiv) in THF (15 ml) was added dropwise to a stirred solution of NaH (370 mg, 12.02 mmol, 2 equiv) in THF (50 ml). After that a solution of allyl bromide (1 ml; 1.45 g, 12.02 mmol, 2 equiv) in THF (5 ml) was added and the mixture obtained was stirred at 80° C. overnight. The reaction mixture was then allowed to cool to rt and water was added, the solvent was removed and the residue obtained was extracted with diethyl ether. The combined organic layers were dried ($MgSO_4$) and the crude product was purified by flash column chromatography (14.3% ethyl acetate-n-hexane) to yield the title compound 2a (2.7 g, 5.76 mmol, 96%); $R_f$ 0.4 (14.3% ethyl acetate-n-hexane).

1.7: Preparation of Alcohol 2b

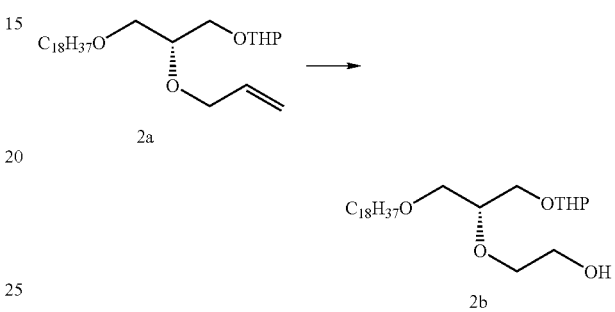

A stirred solution of allyl ether 2a (2.7 g, 5.76 mmol, 1 equiv) in 50% DCM-MeOH (250 ml) at −78° C. was purged with ozone until the mixture showed a blue color. After that $NaBH_4$ (0.9 g, 23.04 mmol, 4 equiv) was added and the mixture obtained was allowed to warm to rt. The reaction was quenched by the addition of water and the mixture obtained was extracted with diethyl ether. The combined extracts were dried. ($MgSO_4$) and the crude product was purified by flash column chromatography (25% ethyl acetate-n-hexane) to yield the title compound 2b (2.64 g, 5.58 mmol, 97%); $R_f$ 0.1 (25% ethyl acetate-n-hexane).

1.8: Preparation of p-Toluene Sulfonyl Ester 3

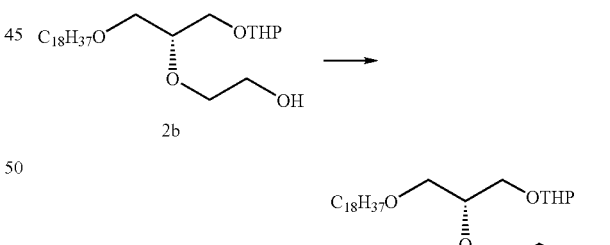

Triethylamine (5 ml) and DMAP (catalytic amount) was added to a stirred solution of alcohol 2b (600 mg, 1.26 mmol, 1 equiv) in DCM (30 ml). To the solution obtained was added a solution of TsCl (360 mg, 1.9 mmol, 1.5 equiv) in DCM (10 ml). After stirring overnight water was added, the mixture obtained was extracted with diethyl ether and the combined organic layers dried ($MgSO_4$). The crude product was purified by flash column chromatography (25% ethyl acetate-n-hexane) to yield the title compound 3 (570 mg, 0.9 mmol, 72%); $R_f$ 0.2 (25% ethyl acetate-n-hexane).

1.9: Synthesis of Pentabenzylinositol 8

1.9.1: Preparation of Acetonide 8a

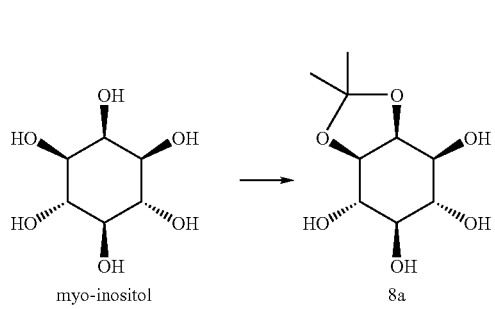

myo-inositol → 8a

Dimethoxypropane (75 ml; 63.75 g, 0.61 mol, 5.5 equiv) und p-TsOH (0.15 g) were added to a stirred suspension of myo-inositol (20 g, 0.11 mol, 1 equiv) in DMSO (75 ml). The mixture obtained was heated to 110° C. and after 1.5 h the MeOH formed was distilled off. Excess dimethoxypropane was removed under reduced pressure. Myo-inositol (20 g, 0.11 mol) was added again and the mixture obtained stirred at 120° C. for further 14 h. After that $K_2CO_3$ (0.15 g) was added and the solvent was removed until a viscous syrup was formed. The syrup was dissolved in boiling EtOH (1.5 l), filtered when still hot and the filtrate was concentrated to a volume of 30 ml. After the product was crystallized the liquor was filtered off, the crystals were washed with EtOH and subsequently subjected 5-times to recrystallization from EtOH to yield 8a (9.91 g, 45 mmol, 41%) as a white solid (excess myo-inositol is not soluble in EtOH and therefore can be recovered easily).

1.9.2: Preparation of Tetrabenzyl Ether 8b

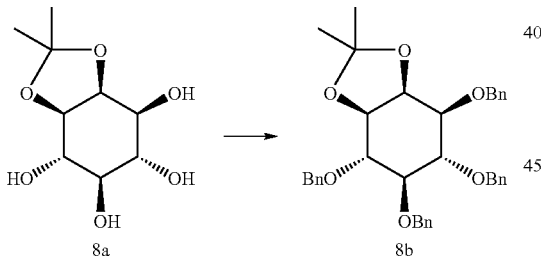

8a → 8b

A stirred solution of Tetrol 8a (1.1 g, 5 mmol, 1 equiv) in DMF (10 ml) was added dropwise to a suspension of NaH (80% dispersion in mineral oil; 0.9 g, 30 mmol, 1.5 equiv) in DMF (10 ml) warmed to 50° C. for a short period of time. After that a solution of benzyl bromide (4.75 ml; 40 mmol, 2 equiv) in DMF (5 ml) was added and the mixture obtained stirred at 80° C. overnight. The reaction mixture was allowed to cool to rt, diluted with the same volume of diethyl ether and washed with saturated aqueous $NaHCO_3$. The aqueous layer was extracted with diethyl ether, the combined organic layers were dried ($MgSO_4$) and the solvent removed. The crude product was purified by flash column chromatography (25% ethyl acetate-n-hexane). Remaining traces of benzyl bromide were removed under reduced pressure to yield the title compound 8b (2.13 g, 3.7 mmol, 73.4%); $R_f$ 0.34 (25% ethyl acetate-n-hexane).

1.9.3: Preparation of Diol 8c

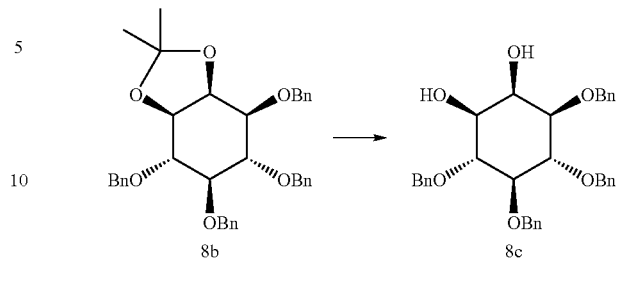

8b → 8c

A solution of acetonide 8b (1.02 g, 1.8 mmol, 1 equiv) in MeOH was adjusted to pH 2 by the addition of aqueous HCl and stirred at rt overnight. After that saturated aqueous $NaHCO_3$ was added to the reaction mixture and the solvent removed under reduced pressure. The residue obtained was dissolved in DCM and dried ($MgSO_4$). The solvent was removed and the crude product recrystallized from MeOH to yield the title compound 8c (0.7 g, 1.3 mmol, 72%); $R_f$ 0.04 (25% ethyl acetate-n-hexane).

1.9.4: Preparation of Allyl Ether 8d

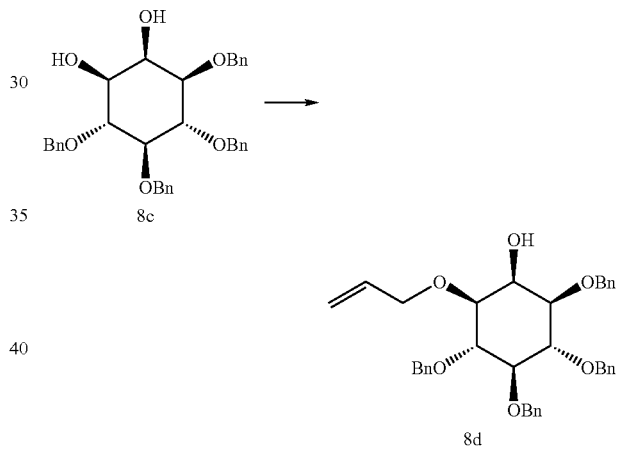

8c → 8d

To a stirred solution of diol 8c (0.45 g, 0.83 mmol, 1 equiv) in toluene (5 ml) was added freshly crushed NaOH (0.45 g) and allyl bromide (0.12 ml, 1.5 mmol, 1.8 equiv). After approximately 2 h (monitoring by thin layer chromatography, 50% ethyl acetate-n-hexane) at 65° C. the reaction mixture was washed with water and dried ($K_2CO_3$). Flash column chromatography (50% ethyl acetate-n-hexane) yielded the title compound 8d (120 mg, 0.21 mmol, 25%); $R_f$ 0.6 (50% ethyl acetate-n-hexane).

1.9.5: Preparation of Pentabenzyl Ether 8e

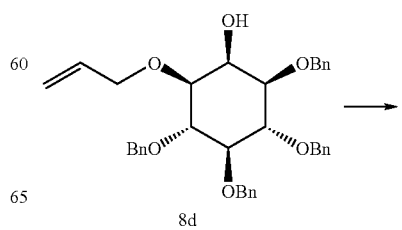

8d

-continued

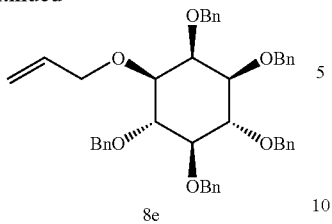

8e

To a stirred mixture of alcohol 8d (1 g, 1.72 mmol, 1 equiv), DMF (3.5 ml) and NaH (80% dispersion in mineral oil; 0.08 g) at 50° C. was added dropwise benzyl bromide (0.33 ml; 0.44 g, 2.6 mmol, 1.5 equiv). The reaction mixture was allowed to cool to rt after approximately 2 h (monitoring by thin layer chromatography, 25% ethyl acetate-n-hexane) followed by the dropwise addition of water. The mixture obtained was extracted with diethyl ether and the combined organic layers were dried (MgSO$_4$) and the solvent removed. The crude product was purified by flash column chromatography (14.3% ethyl acetate-n-hexane) to yield the title compound 8e (1.1 g, 1.64 mmol, 95%); R$_f$ 0.45 (25% ethyl acetate-n-hexane).

1.9.6: Preparation of Pentabenzylinositol 8

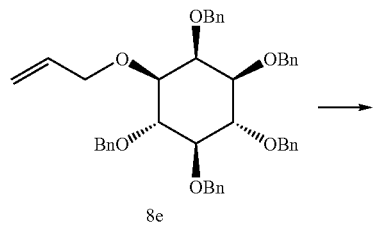

8e

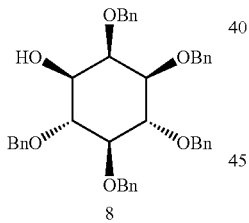

8

A mixture of allyl ether 8e (0.5 g, 0.74 mmol, 1 equiv), 16.7% MeOH-water (6 ml), Pd/C (5%; 20 mg) and p-TsOH (20 mg) was stirred at boiling temperature overnight (for better solubilization 1,4-dioxane can be added). The reaction mixture was allowed to cool to rt and filtered through Celite®. The filtrate was concentrated and purified by flash column chromatography (25% ethyl acetate-n-hexane) to yield the title compound 8 (345 mg, 0.55 mmol, 74%).

1.10: Preparation of Inositol Derivative 4

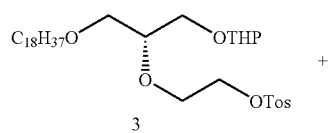

3

-continued

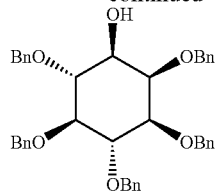

8

4

To a stirred solution of inositol 8 (675 mg, 1.08 mmol, 1.2 equiv) and 18-crown-6 ether (18-Cr-6, 320 mg) in THF (20 ml) was added a KHMDS-solution (15% in THF; 2.4 ml). The mixture obtained was heated at 55° C. for 10 minutes. After that the tosylate 3 (570 mg, 0.9 mmol, 1 equiv) dissolved in THF (20 ml) was added and the mixture obtained was stirred for 30 minutes at 40° C., after which the reaction was quenched by the addition of water. The mixture obtained was extracted with diethyl ether and the combined organic layers were washed with brine and dried (MgSO$_4$). After concentration the crude product was purified by flash column chromatography (25% ethyl acetate-n-hexane) to yield the title compound 4 (690 mg, 0.63 mmol, 70%); R$_f$ 0.25 (25% ethyl acetate-n-hexane).

1.11: Preparation of Alcohol 5

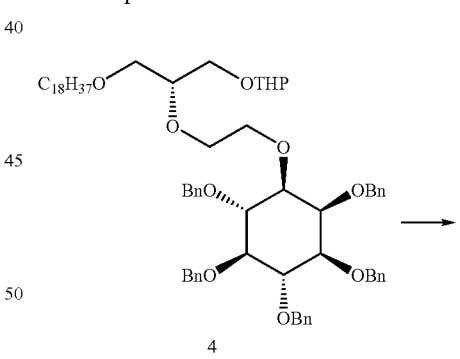

4

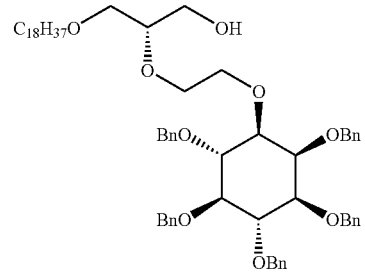

5

To a stirred solution of THP ether 4 (690 mg, 0.63 mmol, 1 equiv) in EtOH (15 ml) was added PPTS (60 mg, 0.1 equiv)

and the mixture obtained was stirred at 55° C. for two hours. The solvent was removed and the crude product was purified by flash column chromatography (25% ethyl acetate-n-hexane) to yield the title compound 5 (510 mg, 0.51 mmol, 81%); $R_f$ 0.1. (25% ethyl acetate-n-hexane).

1.12: Preparation of Phosphocholine 6

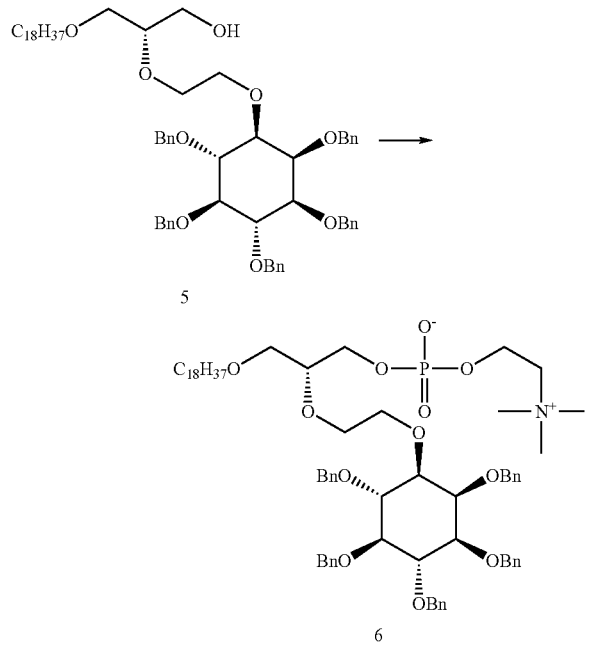

To a stirred solution of POCl$_3$ (0.17 ml, 1.85 mmol, 1.05 equiv) and triethyl amine (1 ml) in DCM (15 ml) at 0° C. was added a solution of alcohol 5 (1.78 g, 1.77 mmol, 1 equiv) in chloroform (15 ml). The mixture obtained was stirred at 0° C. for further 3 hours after which a solution of choline tosylate (0.7 g, 2.66 mmol, 1.5 equiv), in pyridine (50 ml) was added quickly at 0° C. After that the reaction mixture was allowed to warm to rt overnight. The reaction was quenched by the addition of saturated aqueous NaHCO$_3$ until the pH changed to slightly basic, and the mixture obtained was concentrated under reduced pressure at less than 35° C. The residue obtained was dissolved in 50% toluene-DCM (100 ml), filtered and again concentrated. The same procedure was repeated with THF and the crude product finally obtained was further purified by flash column chromatography (17%→100% MeOH-chloroform) to yield the title compound 6 (1.42 g, 1.21 mmol, 68%); $R_f$ 0.1 (100% MeOH).

1.13: Preparation of Pentol 7

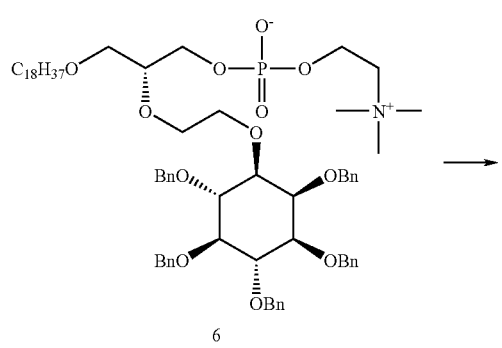

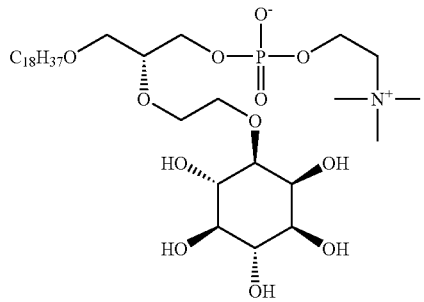

A solution of benzyl ether 6 (1.42 g, 1.21 mmol) in MeOH (15 ml) containing Pd/C (5%; catalytic amount) and acetic acid (catalytic amount) was stirred for three days under an atmosphere of hydrogen (2 bar). The reaction was monitored by thin layer chromatography (100% MeOH), and after the sm could not be detected any more the reaction mixture was filtered through Celite® and the solvent was removed. The filtrate obtained was redissolved in MeOH, filtered through a paper filter and the solvent was removed. The residue was purified through a small pad of silica gel using MeOH for washing. The solvent was again removed and the crude product obtained was redissolved in MeOH. The product was precipitated by the addition of acetone followed by decantation of the supernatant and drying under reduced pressure to yield inositol-C2-PAF 7 (530 mg, 0.74 mmol, 61%); $R_f$<0.1. (100% MeOH); mp 190-210° C. (decomposition); $[\alpha]^{20}_D$ −1.3 (c 1, MeOH).

Example 2

Determination of the Antiproliferative Effect of Ino-PAF

Ino-PAF as obtained in Example 1, Glc-PC and Glc-PAF (synthesis according to Mickeleit, M. et al., Angew. Chem. Int. Ed. Engl. 34:2667-2669 (1995) and 37:351-353 (1998)), and HePC (Hexadecylphosphocholine; commercially available as Miltefosin) were tested in the cell proliferation ELISA, BrdU (col.), Roche in an amount of from 0.6 to 5 µM. Prior to the assay the cells were kept for 2 h in serum-free keratinocyte medium. Assays were performed using 10.000 cells per test, at least quadruple testing.

Figure 2:
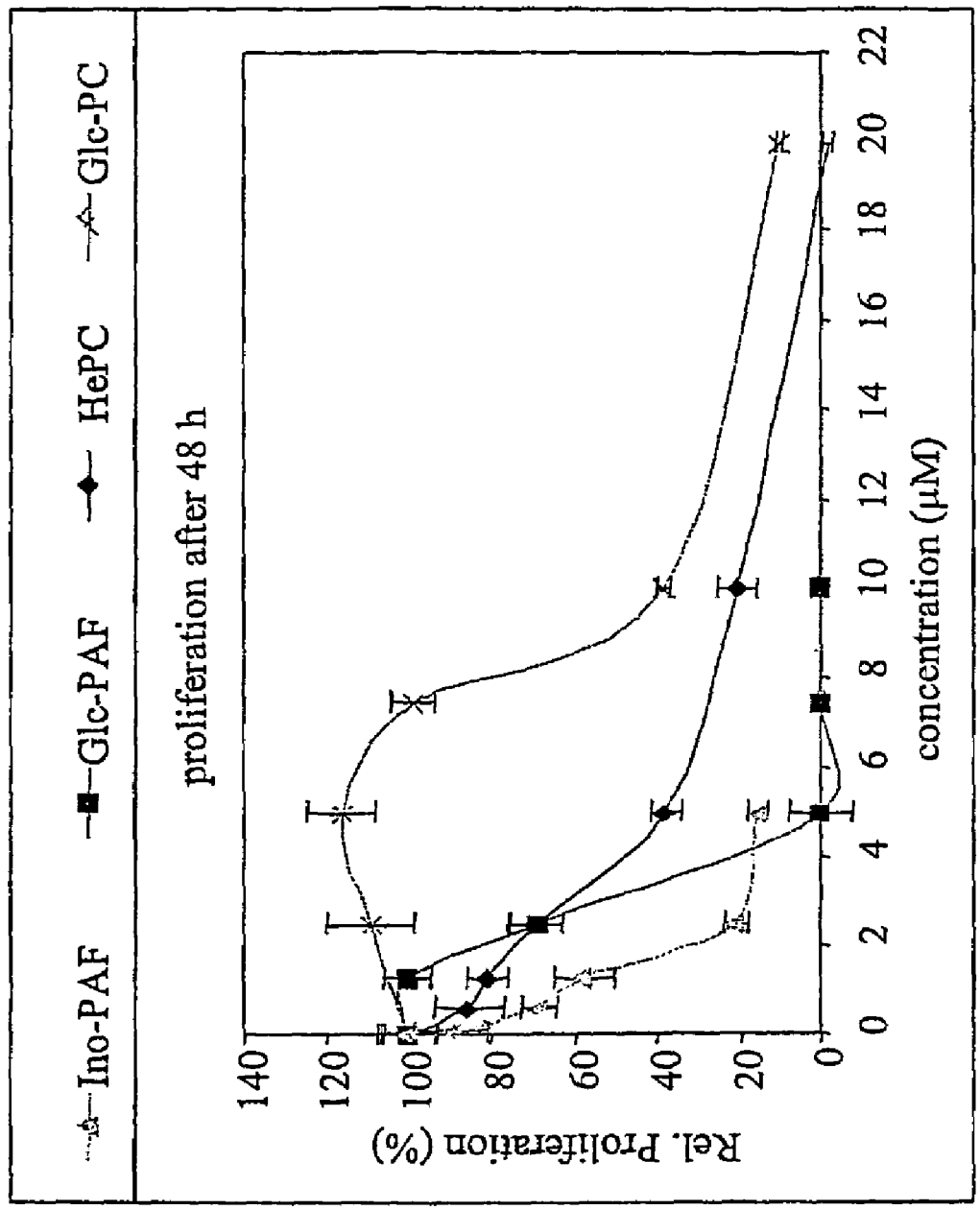
FIG. 2 shows the determination of the antiproliferative effect of Ino-PAF in comparison to other phospholipid analogs according to Example 2.

Ino-PAF and Glc-PC reveal strong antiproliferative effects at non cytotoxic concentrations (FIG. 2).

Example 3

Treatment of HaCaT Cells with Ino-PAF Affects Matrix Adhesion

In order to study the effect of Glc-PAF, Ino-PAF and Glc-PC (as specified in Example 2) on cell matrix adhesion HaCaT cells were rested 15 min at 4° C. and allowed to adhere to different ECM proteins (collagen IV, fibronectin and laminin) for 90 min at 37° C. The proteins of the extracellular matrix (ECM) were loaded onto the plastic surface by overnight treatment at 4° C. After fixing and staining in crystal violet, coloring was measured at 570 nm. Per test were used 50,000 cells, and quadruple testing was performed. Treatment for 2 h shows an increased cell matrix adhesion, after 48 h this cannot be observed any longer.

Incubation with Ino-PAF leads to a concentration-dependent increase of cell-matrix adhesion to the tested matrix proteins, whereas Ino-PAF had the greatest impact on cell-matrix adhesion. The surface expression of integrins, receptors that mediate cell-matrix adhesion is not affected by the substance. The results as shown in FIG. 3 are mean values of at least three experiments done in quadruplicate.

Example 4

Treatment of HaCaT Cells with Ino-PAF

Figure 4:
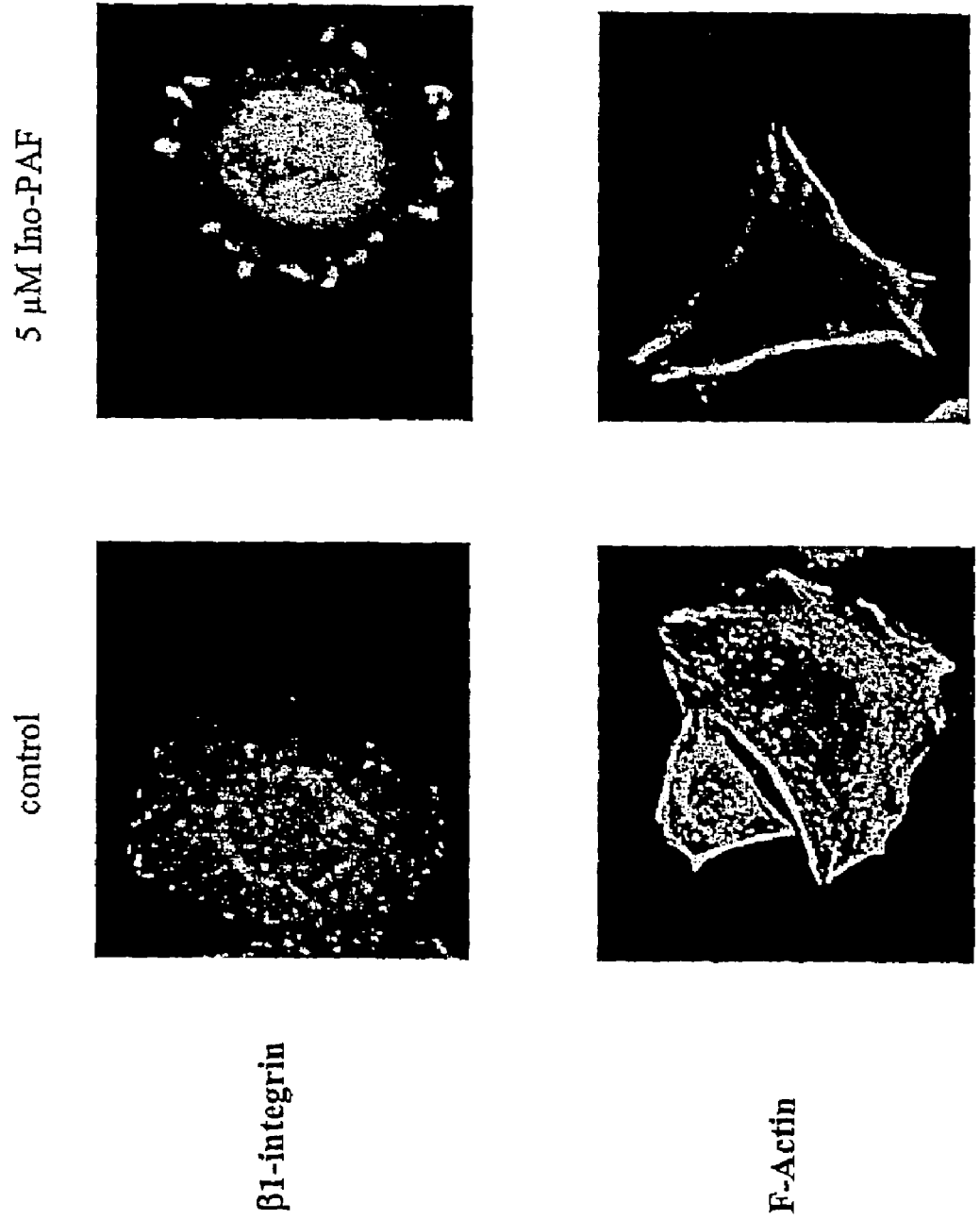
FIG. 4: shows how the treatment of HaCaT cells with Ino-PAF induces integrin clustering and affects the cytoskeleton (treatment and visualization according to Example 4).

HaCaT cells were treated with Ino-PAF (obtained as described in Example 1) for 48 h. For the immunofluorescence measurement, cells were treated with 5 μM Ino-PAF. The antibody utilized for detection was directed against the β1-Integrin, which is a surface receptor conferring cell-matrix-adhesion. Immunofluorescence analysis was performed on a collagen IV matrix. $5 \times 10^4$ cells/well were left to adhere for 90 min and stained with K20-FITC (anti-β1) or Phalloidin-TRITC respectively. The results are shown in FIG. 4.

Example 5

Haptotactic Migration Assay

In order to study the effect of Glc-PAF, Ino-PAF and Glc-PC (as specified in Example 2) on migration haptotactic migration assays with HaCaT cells towards collagene IV were performed. Migration assays were performed using Transwell (Costar Corp., USA) motility chambers. The lower surfaces of the membranes were coated with matrix proteins at room temperature for 30 min and subsequently washed with PBS. $1 \times 10^5$ cells per well were plated in serum-free media on the upper surface and allowed to migrate for 16 h. Cells on the upper surface were removed, and migrated cells on the lower surface were fixed with 3% paraformaldehyde and stained with 0.1% crystal violet. Cells on the lower surface were counted using a 10× grid at 20× magnification. Four fields per filter were counted and averaged.

Migration decreased concentration-dependently. It turned out that the treatment of cells with the test substances decreased matrix-dependent migration up to 50% after 24 h treatment.

The invention claimed is:

1. A phospholipid according to formula I having a substituted or unsubstituted polyhydroxylated aliphatic carbocycle attached to the sn-2 position of the glycerol backbone wherein

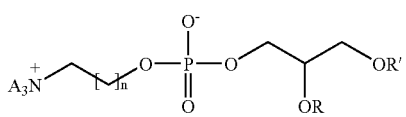

(I)

(i) A are independently optionally substituted $C_{1-6}$ alkyl moieties or two A residues may form an optionally substituted 5- to 10-membered ring, (ii) R is a polyhydroxylated aliphatic carbocycle or a derivative thereof being directly or through a linker molecule connected to the oxygen atom of the glycerol backbone, (iii) R' is selected from the group consisting of (i) optionally unsaturated and/or optionally substituted $C_{1-20}$ alkyl, (ii) optionally unsaturated and/or optionally substituted $C_{2-26}$ acyl and (iii) hydrogen, and (iv) n is an integer ranging from 1 to 5.

2. The phospholipid of claim 1 wherein A is selected from the group consisting of $CH_3$, $C_2H_5$, $C_3H_7$ and $CH(CH_3)_2$.

3. The phospholipid of claim 2 wherein A is $CH_3$.

4. The phospholipid of claim 1 wherein R' is a $C_{10-20}$ alkyl group.

5. The phospholipid of claim 4 wherein R' selected from the group consisting of a $C_{16}$ alkyl group and a $C_{18}$ alkyl group.

6. The phospholipid of claim 1 wherein R is a member selected from the group of formulas consisting of formulas (II) to (IV):

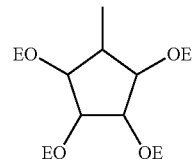

(II)

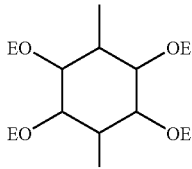

(III)

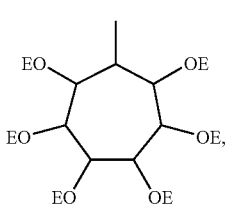

(IV)

wherein E is selected from the group consisting of H, $C_{1-4}$ alkyl, $C_{2-4}$ acyl and a carbohydrate moiety 7. The phospholipid of claim 6 wherein E is H.

8. The phospholipid of claim 6 wherein R is a residue of formula (III).

9. The phospholipid of claim 1, wherein a linker L connecting R to the glycerol backbone is selected from the group consisting of a (poly)ether, (poly)peptide and glycoside.

10. The phospholipid of claim 9 wherein a linker L is a (poly)ether.

11. The phospholipid of claim 1 wherein n=1.

12. The phospholipid of claim 8 wherein the residue of formula (III) is selected from the group consisting of cis-inositol, epi-inositol, allo-inositol, neo-inositol, myo-inositol, muco-inositol, chiro-inositol and scyllo-inositol.

13. The phospholipid of claim 12 wherein the residue of formula (III) is myo-inositol.

14. The phospholipid of claim 1 which corresponds to formula (V)

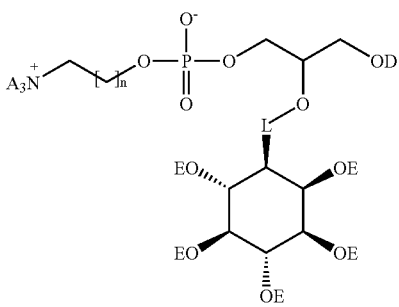

(V)

wherein

D is selected from the group consisting of optionally unsaturated and/or optionally substituted $C_{1-20}$ alkyl, optionally unsaturated and/or optionally substituted $C_{2-26}$ acyl and hydrogen, E is selected from the group consisting of H, $C_{1-4}$ alkyl, $C_{2-4}$ acyl and a carbohydrate moiety, A is selected from the group consisting of $CH_3$, $C_2H_5$, $C_3H_7$ and $CH(CH_3)_2$, n is an integer from 1 to 5, and L is a chemical bond, a linker selected from the group consisting of a (poly)ether linker, (poly)peptide linker and a glycoside linker.

15. The phospholipid of claim 14 wherein A is $CH_3$, n is 1, L is —$CH_2CH_2$—O—, D is $C_{18}H_{37}$ and E is H.

16. A pharmaceutical composition comprising a phospholipid according to claim 1.

17. The pharmaceutical composition of claim 16 which is suitable for the inhibition of cell proliferation, modulation of cell-cell and cell-matrix adhesion, as an anticancer agent or inhibition of cell migration.

18. A method for preparing a compound of claim 1, which method comprises reacting a glycerol precursor compound with a precursor of the compound of the activated substituted or unsubstituted polyhydroxylated aliphatic carbocycle.

19. A method of inhibiting cell proliferation for treating a disease selected from the group consisting of prostate carcinoma, urothelial carcinoma of the bladder, hypernephroid carcinoma, teratocarcinomas, human and murine leukemias, brain tumors, lung cancers, fibrosarcomas and hyperproliferation diseases of the skin, which method comprises administering a therapeutically effective amount of a compound of claim 1, to a subject in need of such treatment.

\* \* \* \* \*